US007899194B2

(12) United States Patent
Boesen

(10) Patent No.: US 7,899,194 B2
(45) Date of Patent: Mar. 1, 2011

(54) DUAL EAR VOICE COMMUNICATION DEVICE

(76) Inventor: Peter V. Boesen, Des Moines, IA (US)

( * ) Notice: Subject to any disclaimer, the term of this patent is extended or adjusted under 35 U.S.C. 154(b) by 1091 days.

(21) Appl. No.: 11/251,279

(22) Filed: Oct. 14, 2005

(65) Prior Publication Data

US 2007/0086600 A1 Apr. 19, 2007

(51) Int. Cl.

| | |
|---|---|
| ***A61F 11/06*** | (2006.01) |
| *H04B 3/00* | (2006.01) |
| *H04R 25/00* | (2006.01) |
| *H04R 25/02* | (2006.01) |
| *A61B 7/02* | (2006.01) |
| *H04M 1/00* | (2006.01) |

(52) U.S. Cl. .......................... 381/79; 381/77; 381/380; 381/375; 181/130; 181/135; 455/556.1; 455/556.2

(58) Field of Classification Search ..................... 381/1, 381/312, 380

See application file for complete search history.

(56) References Cited

U.S. PATENT DOCUMENTS

| | | | | |
|---|---|---|---|---|
| 3,934,100 | A | 1/1976 | Harada | |
| 3,985,960 | A * | 10/1976 | Wallace, Jr. | 381/309 |
| 4,150,262 | A | 4/1979 | Ono | |
| 4,334,315 | A | 6/1982 | Ono et al. | |
| 4,375,016 | A | 2/1983 | Harada | |
| 4,588,867 | A | 5/1986 | Konomi | |
| 4,654,883 | A | 3/1987 | Iwata | |
| 4,682,180 | A | 7/1987 | Gams | |
| 4,791,673 | A | 12/1988 | Schreiber | |

(Continued)

FOREIGN PATENT DOCUMENTS

GB 2 074 817 A 11/1981

(Continued)

OTHER PUBLICATIONS

Jeff Foerster,EvanGreen, Srinivasa Somayazulu, David Leeper "Ultra- Wideband Technology for Short-or Medium- Range Wireless Communication", http://www.intel.com/technology/itj/q22001/pdf/art_4.pdf, 2001, pp. 1-3.*

(Continued)

*Primary Examiner*—Curtis Kuntz
*Assistant Examiner*—Sunita Joshi
(74) *Attorney, Agent, or Firm*—Mckee, Voorhees & Sease, P.L.C.

(57) ABSTRACT

A method for voice communication which includes sensing at least one channel of audio information from proximate a first external auditory canal of a user, sensing at least one channel of audio information proximate a second external auditory canal of the user, and wirelessly transmitting the at least one channel of audio information from proximate the first external auditory canal of the user and the at least one channel of audio information from proximate the second external auditory canal of the user. The method may further include producing a stereophonic audio signal based on the at least one channel of audio information from proximate the first external auditory canal and the at least one channel of audio information from proximate the second external auditory canal. The signal may be stereophonic, recognize right or left, and be tailored to fit the audiometric needs of the user.

25 Claims, 6 Drawing Sheets

U.S. PATENT DOCUMENTS

| | | | | | |
|---|---|---|---|---|---|
| 5,191,602 | A | | 3/1993 | Regen et al. | |
| 5,201,007 | A | | 4/1993 | Ward et al. | |
| 5,280,524 | A | | 1/1994 | Norris | |
| 5,295,193 | A | | 3/1994 | Ono | |
| 5,298,692 | A | | 3/1994 | Ikeda et al. | |
| 5,343,532 | A | | 8/1994 | Shugart, III | |
| 5,606,621 | A | | 2/1997 | Reiter et al. | |
| 5,613,222 | A | | 3/1997 | Guenther | |
| 5,692,059 | A | | 11/1997 | Kruger | |
| 5,721,783 | A | * | 2/1998 | Anderson | 381/328 |
| 5,771,438 | A | | 6/1998 | Palermo et al. | |
| 5,802,167 | A | | 9/1998 | Hong | |
| 5,933,506 | A | | 8/1999 | Aoki et al. | |
| 5,949,896 | A | | 9/1999 | Nageno | |
| 5,987,146 | A | | 11/1999 | Pluvinage et al. | |
| 6,021,207 | A | | 2/2000 | Puthuff et al. | |
| 6,094,492 | A | | 7/2000 | Boesen | |
| 6,112,103 | A | | 8/2000 | Puthuff | |
| 6,181,801 | B1 | | 1/2001 | Puthuff et al. | |
| 6,549,633 | B1 | * | 4/2003 | Westermann | 381/312 |
| 7,039,195 | B1 | * | 5/2006 | Svean et al. | 381/71.6 |
| 7,519,194 | B2 | * | 4/2009 | Niederdrank et al. | 381/330 |
| 2001/0024507 | A1 | * | 9/2001 | Boesen | 381/315 |
| 2005/0078844 | A1 | * | 4/2005 | Von Ilberg | 381/322 |
| 2005/0113136 | A1 | * | 5/2005 | Gosieski | 455/556.1 |
| 2005/0283263 | A1 | * | 12/2005 | Eaton et al. | 700/94 |

FOREIGN PATENT DOCUMENTS

| | | | | |
|---|---|---|---|---|
| JP | 06-292195 | | | 10/1994 |
| WO | WO 0154458 | A2 | * | 7/2001 |
| WO | WO 2004110099 | A2 | * | 12/2004 |

OTHER PUBLICATIONS

"U.S. Will Oversee Cell-Phone Safety Studies", www.cmpnet.com REU20000609S0003, Jun. 9, 2000.

"Wireless Worries: Are Cell Phones a Danger to You and Your Children", ABC News May 26, 2000.

"A One-Size Disposable Hearing Aid is introduced", Staab, Wayne J., et al., The Hearing Journal, Apr. 2000, vol. 53, No. 4, pp. 36-41.

"Blue Tooth Usage Model" The Official Bluetooth Website www.bluetooth.com/bluetoothguide/models/ultimate.asp (visted Jun. 26, 2000).

"Scientists link eye cancer to mobile phones" by Jonathan Leake, The Sunday Times: New Jan. 14, 2001.

"Brain cancer victim sues cell-phone providers" www:CNN.com/2000/TECH/computing/08/08/cellular.cancer.lawsuit.idg/index.html Aug. 8, 2000.

"Report Urges Curbs on Mobile Phone Use" by Ian Cameron, Electronics Times May 15, 2000 www.techweb.com/wire/story/TWB20000515S005.

"The Hearing Review", Jan. 1999, vol. 3: Hearing in Noise (Supplemental), pp. 1-62.

"What is a Wireless LAN?" White Paper PROXIM Mar. 1998.

* cited by examiner

DUAL EAR VOICE COMMUNICATION DEVICE

BACKGROUND OF THE INVENTION

The present invention provides for binaural and/or stereophonic sensing and reproduction of sound. In binaural recording, a pair of microphones is placed inside a model of a human head which includes external ears and ear canals. Each microphone is placed approximately where the ear drum is located. The recording is then played back through headphones, to maintains separate channels without mixing or crosstalk. Thus, each of the listener's tympanic membrane is driven with a replica of the auditory signal it would have experienced at the recording location. The result is an accurate duplication of the auditory spatiality that would have been heard by the listener placed where the microphones were located. True binaural recordings have remained laboratory and audiophile curiosities and have not been adopted.

A seemingly unrelated problem exists with respect to handsfree devices. Numerous advantages are associated with handsfree devices which make them desirable in various situations, including when they are used in combination with cell phones. In addition, the use of handsfree devices can promote privacy, to some extent. Despite these well-recognized advantages and benefits of handsfree devices, problems remain. Due to the discomfort of handsfree devices, and the need to hear environmental devices, handsfree devices to date have focused on reproducing sound in only one ear.

BRIEF SUMMARY OF THE INVENTION

Therefore, it is a primary object, feature, or advantage of the present invention to improve over the state of the art.

It is a further object, feature, or advantage of the present invention to provide a voice communication system that provides for transducing and playing multi-channel audio using an earpiece.

It is a still further object, feature, or advantage of the present invention to provide a voice communication system that provides for binaural transducing and playing of audio.

Yet a further object, feature, or advantage of the present invention to provide a voice communication system that provides for stereophonic transducing and playing of audio.

It is a further object, feature, or advantage of the present invention is to provide for binaural or stereophonic listening without the nuisance of head phones or any linking material spanning the head from the right earpiece to the left earpiece.

Yet another object, feature, or advantage is to provide for binaural or stereophonic listening with a handsfree device.

A further object, feature, or advantage of the present invention is to provide for transducing, processing of, and playback of voice sound information.

A still further object, feature, or advantage of the present invention is to use a phone to control one or more earpieces.

A still further object, feature, or advantage of the present invention is to take into account head size of a user.

Another object, feature, or advantage of the present invention is to allow for multiple output transducers in an earpiece.

Another object, feature, or advantage of the present is to provide for tracking of a user's head movement.

Yet another object, feature, or advantage of the present invention is to use the speaker of an electronic device such as a cell phone in combination with one or more earpieces.

A further object, feature, or advantage of the present invention is to allow audiometrics of an incoming signal to be modified according to a user's specific audiometric demands.

A still further object, feature, or advantage of the present invention is to communicate whether a signal is coming from a right earpiece or a left earpiece.

One or more of these and/or other objects, features, and advantages of the present invention will become apparent from the specification and claims that follow.

According to one aspect of the present invention, a method for voice communication is provided. The method includes sensing at least one channel of audio information proximate a first external auditory canal of a user, sensing at least one channel of audio information proximate a second external auditory canal of the user, and wirelessly transmitting the at least one channel of audio information from proximate the first external auditory canal and the at least one channel of audio information from proximate the second external auditory canal. Preferably the method includes producing a stereophonic audio signal based on the at least one channel of audio information from proximate the first external auditory canal and the at least one channel of audio information from proximate the second external auditory canal. The stereophonic audio signal may be transduced at a personal electronic device such as a phone or entertainment device or computer. The method may further include receiving the at least one channel of audio information from proximate the first external auditory canal and receiving the at least one channel of audio information from proximate the second external auditory canal at a personal electronic device, producing a stereophonic audio signal based on the at least one channel of audio information from proximate the first external auditory canal and the at least one channel of audio information from proximate the second external auditory canal at the personal electronic device, wirelessly transmitting the stereophonic audio signal from the personal electronic device to a second personal electronic device, transmitting the stereophonic audio signal from the second personal electronic device to one or more devices associated with the ears of a second user, reproducing the at least one channel of audio information from proximate the first external auditory canal of a user proximate a first auditory canal of a second user and reproducing the at least one channel of audio information from proximate the second external auditory canal of the user proximate a second auditory canal of a second user.

According to another aspect of the present invention, a method for stereophonic voice communication between a first user and a second user includes sensing at least one channel of audio information from within a first external auditory canal of the first user, sensing at least one channel of audio information from within a second external auditory canal of the first user, wirelessly transmitting the at least one channel of audio information from within the first external auditory canal of the first user and the at least one channel of audio information from within the second external auditory canal of the first user, outputting at least one channel of audio information within a first external auditory canal of the second user, and outputting at least one channel of audio information within a second external auditory canal of the second user. The step of sensing at least one channel of audio information from within a first external auditory canal of the first user is preferably performed using a microphone position at least partially within the first external auditory canal of the first user. The step of outputting at least one channel of audio information within the first external auditory canal of the second user is preferably performed using a speaker placed within the first external auditory canal of the second user.

According to another aspect of the present invention, a method includes collecting a stereophonic representation of sound associated with a first user, sending the stereophonic representation of sound to a voice communication device associated with the first user, sending the stereophonic representation of sound from the voice communication device to a second user, and playing the stereophonic representation of sound for the second user. The collecting a stereophonic representation of sound may be performed using one or more sensors positioned at or near or proximate the external auditory canal of the user. The step of playing the stereophonic representation of sound for the second user may be performed using one or more speakers positioned at or near or proximate the external auditory canal of the user. The step of collecting a stereophonic representation of sound may be performed using one or more sensors positioned within the external auditory canal of the user. The step of playing the stereophonic representation of sound for the second user may be performed using one or more speakers positioned within the external auditory canal of the user.

According to another aspect of the present invention, a communication system is provided which includes a personal electronic device adapted for sending and receiving stereophonic information, a left earpiece and a right earpiece, each having a speaker and a microphone and each being shaped to position the speaker and the microphone within or at or near an external auditory canal of a user. The personal electronic device may be a phone and/or an entertainment device, a PDA, or a computer. Preferably, the personal electronic device includes a short range transceiver adapted for sending and receiving the stereophonic information to a short range transceiver associated with at least one of the left earpiece and the right earpiece.

According to another aspect of the invention a communication system is provided. The communication system includes a personal electronic device adapted for sending and receiving stereophonic information, a left earpiece and a right earpiece, each having a speaker and a microphone and each being shaped to position the speaker and the microphone proximate an external auditory canal of a user. The personal electronic device may be a phone or may include a short range transceiver adapted for sending and receiving the stereophonic information to a short range transceiver associated with at least one of the left earpiece and the right earpiece. The left earpiece is preferably programmed for use in a left external auditory canal of the user and the right earpiece is preferably programmed for use in a right external auditory canal of the user.

According to another aspect of the present invention, an earpiece adapted for use in a stereophonic system is provided. The earpiece includes a housing, a speaker, at least one input sensor, a processor disposed within the earpiece, the speaker and the at least one input sensor operatively connected to the processor, and a transceiver operatively connected to the processor. The earpiece is adapted to communicate whether the earpiece is associated with a right ear of the user or a left ear of the user using the transceiver. Preferably, the processor is adapted to adjust an audio signal received from the transceiver according to audiometric preferences associated with the user.

According to another aspect of the present invention, an earpiece is provided. The earpiece includes a housing, a speaker, at least one input sensor, and a processor disposed within the earpiece. The speaker and the at least one input sensor are operatively connected to the processor. A transceiver is operatively connected to the processor. The earpiece is associated with a right ear setting or a left ear setting and is adapted to adjust an audio signal received from the transceiver based on whether the earpiece is associated with the right ear setting or the left ear setting. Preferably, the processor is adapted to adjust the audio signal received from the transceiver according to audiometric preferences associated with the user.

DETAILED DESCRIPTION OF THE PREFERRED EMBODIMENT

The present invention will be described as it applies to its preferred embodiment. It is not intended that the present invention be limited to the described embodiment. It is intended that the invention cover all modifications and alternatives which may be included within the spirit and scope of the invention. The present invention provides for binarual and/or stereophonic sensing and reproduction of sound by sensing sounds within the external auditory canal of a user and reproducing sounds within both external auditory canals of a user.

Figure 1:
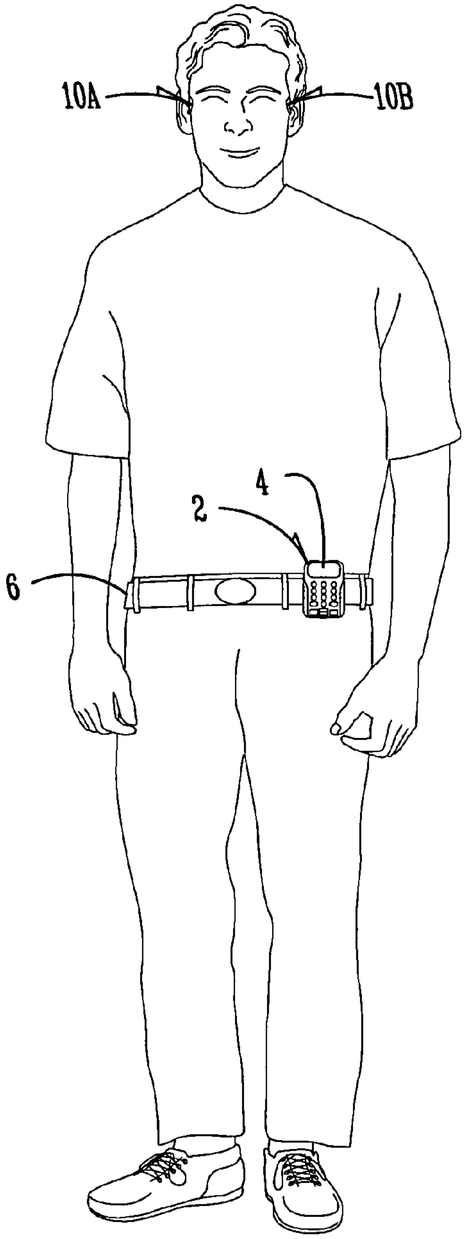
FIG. 1 is a diagram of a personal electronic device worn by a person according to the present invention.

FIG. 1 shows a personal electronic device 2 associated with a person. The personal electronic device may be a phone, an entertainment device, or other type of personal electronic device or computer. The device as shown has a display 4. The device may be worn on a belt 6 as shown or may be placed in a pocket or may be carried by the person. The personal electronic device 2 is in operative communication with earpiece 10A and earpiece 10B. As will be explained in further detail, this configuration provides for the ability to collect and reproduce stereophonic sound.

Figure 2:
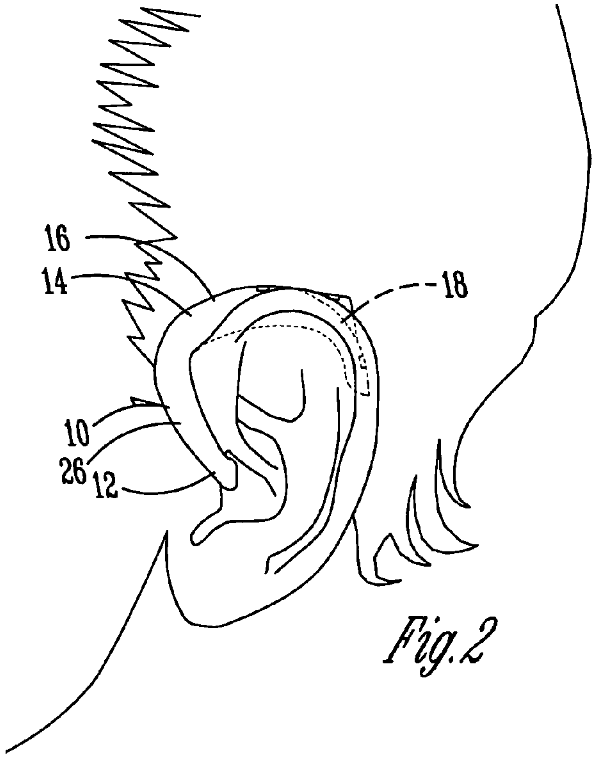
FIG. 2 is a representation of the earpiece of the present invention fitted on the ear.

FIG. 2 shows a pictorial representation of the earpiece 10 as worn in a person's ear. The earpiece has an external ear canal portion 12 which is fitted within the ear. The earpiece 10 has an ear attachment portion 14 fitted around the ear. The earpiece 10 in its preferred form houses a processor 16 and a transceiver 18. The earpiece 10 also houses at least one sensor such as an air conduction sensor or a bone conduction sensor and a speaker. The earpiece 10 corresponds to one of earpiece 10A and earpiece 10B shown in FIG. 1.

Figure 3:
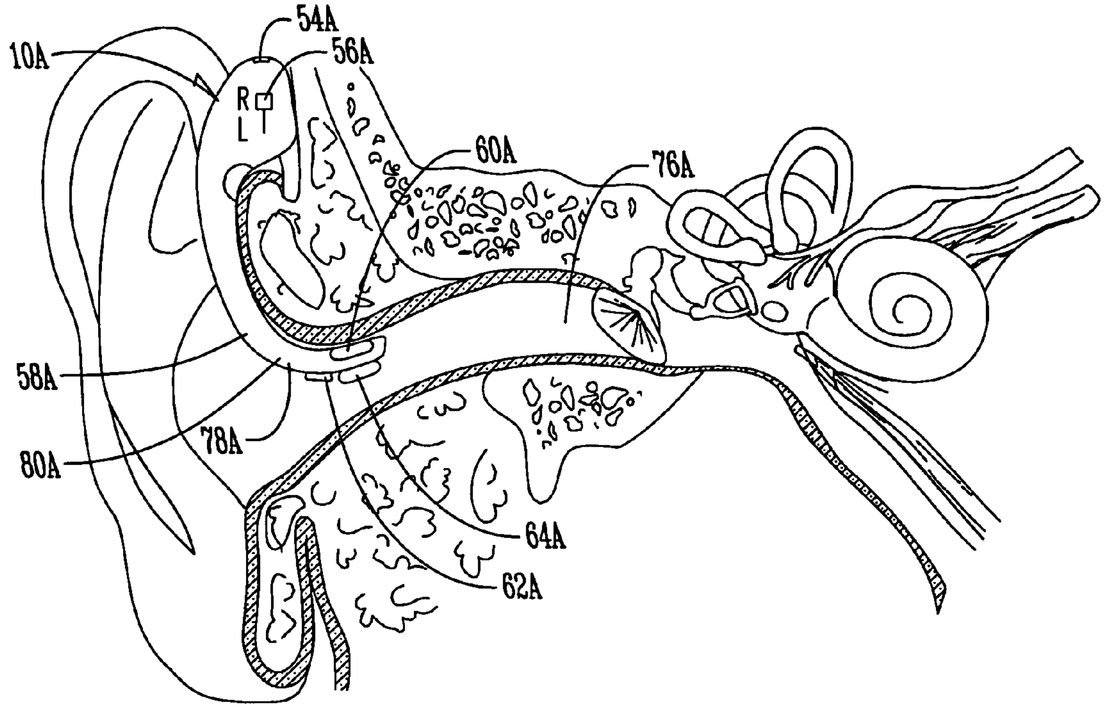
FIG. 3 is a diagram of one embodiment of an earpiece of the present invention fitted within a right ear of a user.

FIG. 3 discloses an example of the earpiece 10A of the present invention having a housing 80A. The earpiece 10A is designed to be worn at the ear. As shown in FIG. 3, an external canal portion 58A of the earpiece 10A is positioned in the external auditory canal 76A of the user. The external auditory canal portion of the earpiece preferentially includes a bone conduction sensor 60A and an air conduction sensor 62A located on a resilient member 78A. An internal antenna 54A is also shown. A speaker 64A is also shown which is also preferably positioned within the external auditory canal 76A of the user. Note that the earpiece 10A of the preferred embodiment does not occlude or block the external auditory canal 76A of the user. This feature increases the comfort of the user so that the user can wear the earpiece for an extended period of time. Also, this feature is important in that it allows the user to also hear environmental sounds. These features are particularly important as the user will be wearing two earpieces to provide for binaural or stereophonic communications. The earpiece may be programmed to compensate for auditory deficits of the user providing amplification, gain or compression as necessary to fit the specific audiometric requirements of the user. In addition, the earpiece may be programmed to accommodate preferences of the user that are not based on the auditory deficits of the user. There is a manual input such as a switch 56A shown that can be used to set the earpiece as a right ear or a left ear. Instead of a hardware setting, the setting can be a software setting or switch.

Figure 4:
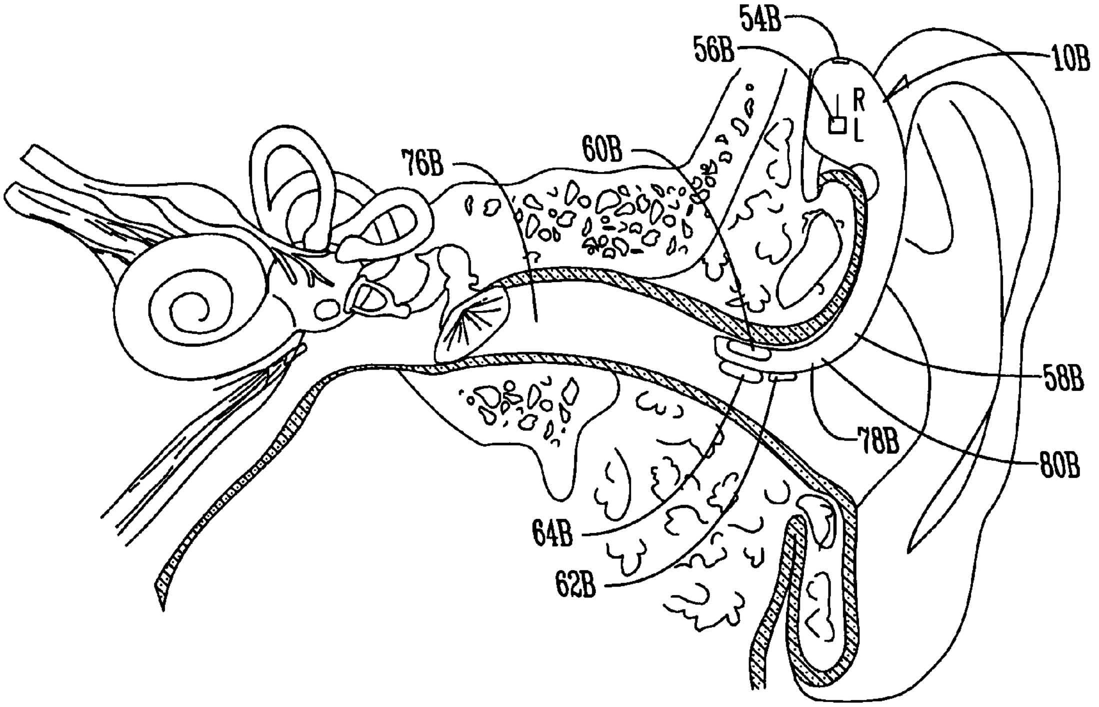
FIG. 4 is a diagram of one embodiment of an earpiece of the present invention fitted within a left ear of a user.

FIG. 4 discloses an example of an earpiece which is substantially identical to earpiece 10A of FIG. 3 but is placed in the opposite ear of the same user. FIG. 4 discloses an example of the earpiece 10B of the present invention having a housing 80B. The earpiece 10B is designed to be worn at the ear. As shown in FIG. 4, an external canal portion 58B of the earpiece 10B is positioned in the external auditory canal 76B of the user. The external auditory canal portion of the earpiece includes a bone conduction sensor 60B and an air conduction sensor 62B located on a resilient member 78B. An internal antenna 54B is also shown. A speaker 64B is also shown which is also preferably positioned within the external auditory canal 76B of the user. In addition, the earpiece may be programmed to accommodate preferences of the user that are not based on the auditory deficits of the user. There is a manual input such as a switch 56B shown that can be used to set the earpiece as a right ear or a left ear. Instead of a hardware setting, the setting can be a software setting or switch.

Figure 5:
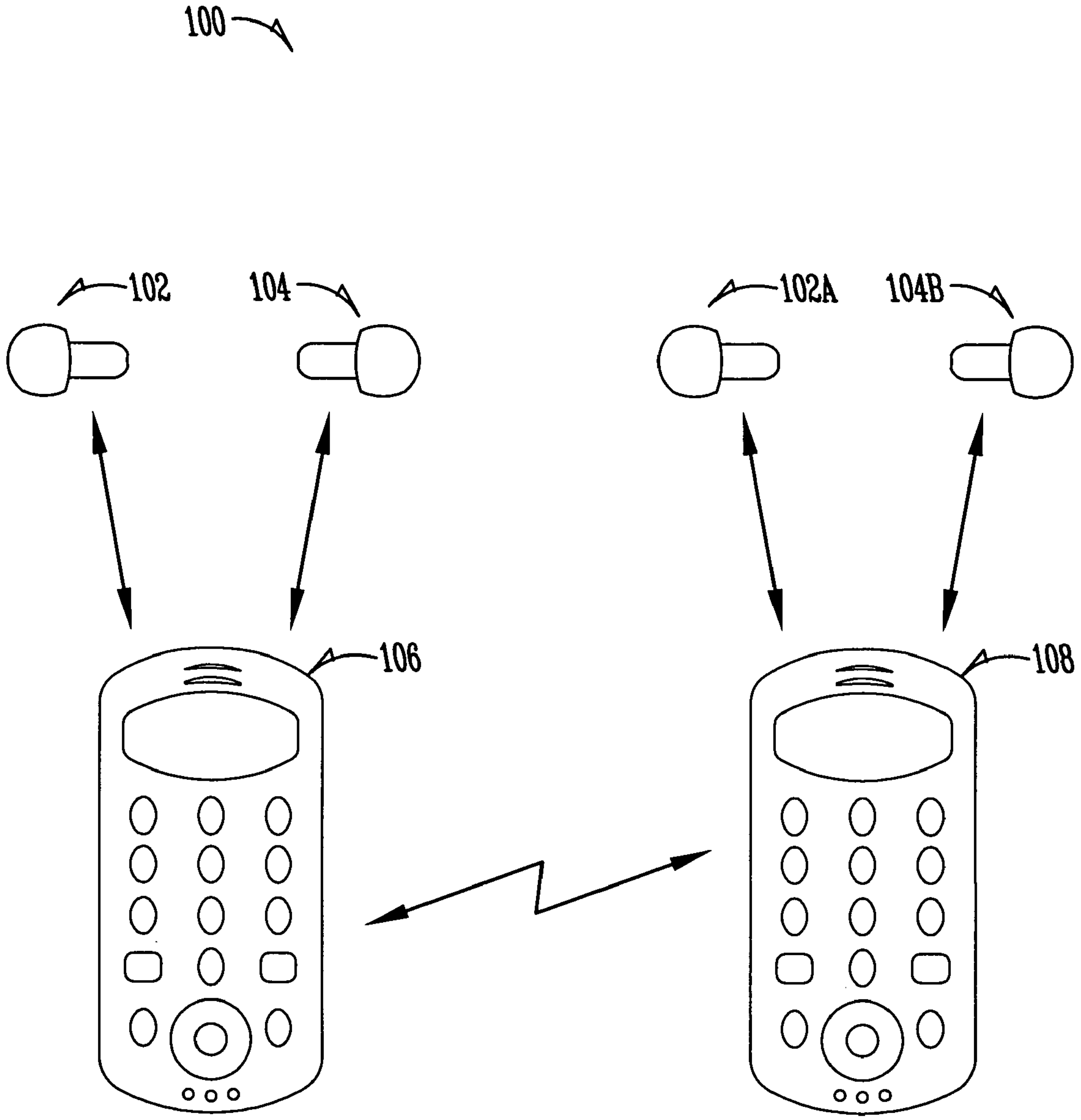
FIG. 5 is a pictorial representation of one embodiment of the present invention.

FIG. 5 discloses an example of one methodology of the present invention. In the system 100 shown in FIG. 5, there is a first earpiece 102 and a second earpiece 104, both earpieces associated with a first user. The earpieces shown are of a completely-in-canal (CIC), although the present invention can be used with behind-the-ear (BTE) or other types of earpieces. Preferably, the earpieces collect sound at or near the external auditory canal of the user and also reproduce sound at or near the external auditory canal of the user. The earpieces 102, 104 are in operative communication with a personal electronic device such as a phone 106. Each of the earpieces 102, 104 communicates one or more channels of audio information to the phone 106 and the phone 106 is adapted to communicate at least one channel of audio information to each earpiece. Thus, when used together, the earpieces 102, 104 provide for collecting stereophonic sound and reproducing stereophonic sound. It should also be appreciated that where stereophonic sound is not needed, only one of the earpieces may be used.

Each of the earpieces 102, 104 is preferably associated with a particular ear of the user. The present invention contemplates that this association can be made in a number of different ways. For example, each earpiece 102, 104 can communicate an identifier to state that it is the left earpiece or a right earpiece as a part of a communications protocol. Alternatively, each earpiece will only receive signals associated with its particular identity. The setting for each earpiece can be accomplished manually (such as a small switch located anywhere on the housing) and/or through programming of the processor within each earpiece. When each earpiece 102, 104 is associated with a particular ear of a user, then processing can also be performed on incoming audio signals to process the incoming audio signal according to the auditory capabilities of a particular user such as may be associated with a hearing aid or according to their auditory preferences. It should also be understood that because the earpiece 102, 104 is a communications device, different types of processing can be performed based on the source of the audio. For example, music received at the earpiece 102, 104 may be processed differently than a telephone call. Or a telephone call from one source may be processed differently than a telephone call from another source.

Because stereophonic sound is easily collected and reproduced at each earpiece, the present invention provides for communicating that stereophonic sound between users. For example, as shown in FIG. 5, stereophonic information can be communicated from phone 106 to a second phone 108 associated with a different user. This stereophonic information can then be transmitted to a second set of earpieces 102A, 104B, to provide stereo sound for the second user.

Figure 6:
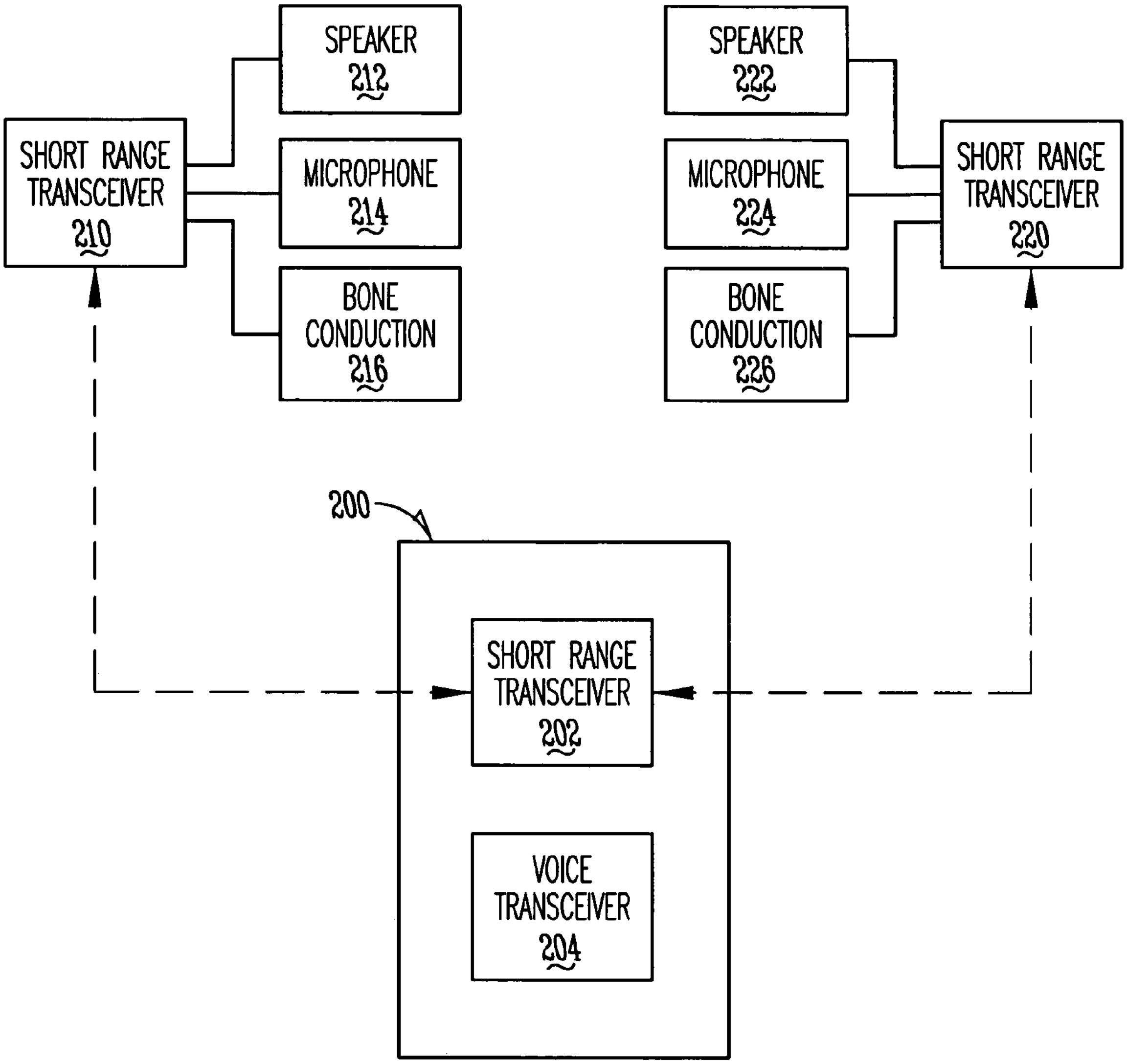
FIG. 6 is a block diagram of another embodiment of the present invention.

It should be understood that although FIG. 5 and FIG. 6 show a preferred embodiment where input sensors and a speaker are positioned directly within the external auditory canal of a user, this is not required. Instead the input sensors and speaker can be placed at or near the external auditory canal or proximate the external auditory canal. There is, however, some advantage in placement within the external auditory canal in that such placement allows for a closer approximation of binaural audio where audio is sensed and played back within the external auditory canal.

FIG. 6 is a block diagram showing another embodiment of the present invention. In FIG. 6, a personal electronic device 200 is shown. The personal electronic device 200 may be a personal communication device, such as a phone, a personal entertainment device, or other type of personal electronic device or computer. The personal electronic device has a short range transceiver 202 and an audio source 204. The audio source 204 may be provided by a voice transceiver for cellular communications, audio received from a stereo transmission associated with radio or television, or from audio created based on stored information. The short range transceiver 202 may be a BLUETOOTH, ultra-wideband (UWB), Wi-Fi or other type of short range transceiver.

The short range transceiver 202 of the personal electronic device 200 is in operative communication with short range transceiver 210 associated with a first earpiece and also associated with a speaker 212, a microphone 214, and an optional bone conduction sensor 216. The short range transceiver 202 of the personal electronic device 200 is also, preferably in operative communication with a second short range transceiver 220 associated with a second earpiece and also associated with a speaker 222, microphone 224, and an optional bone conduction sensor 226. Each earpiece can adjust the incoming signal to fit or adapt to the audiometric needs of the user. This can include auditory deficits of the user such as the type of processing typically performed by various hearing aids. This can also include preferences which can be set by the source or type of audio (such as but limited to music, audio accompanying video, audio associated with a phone call, audio associated with a phone call with a particular person, or other type of audio).

Figure 7:
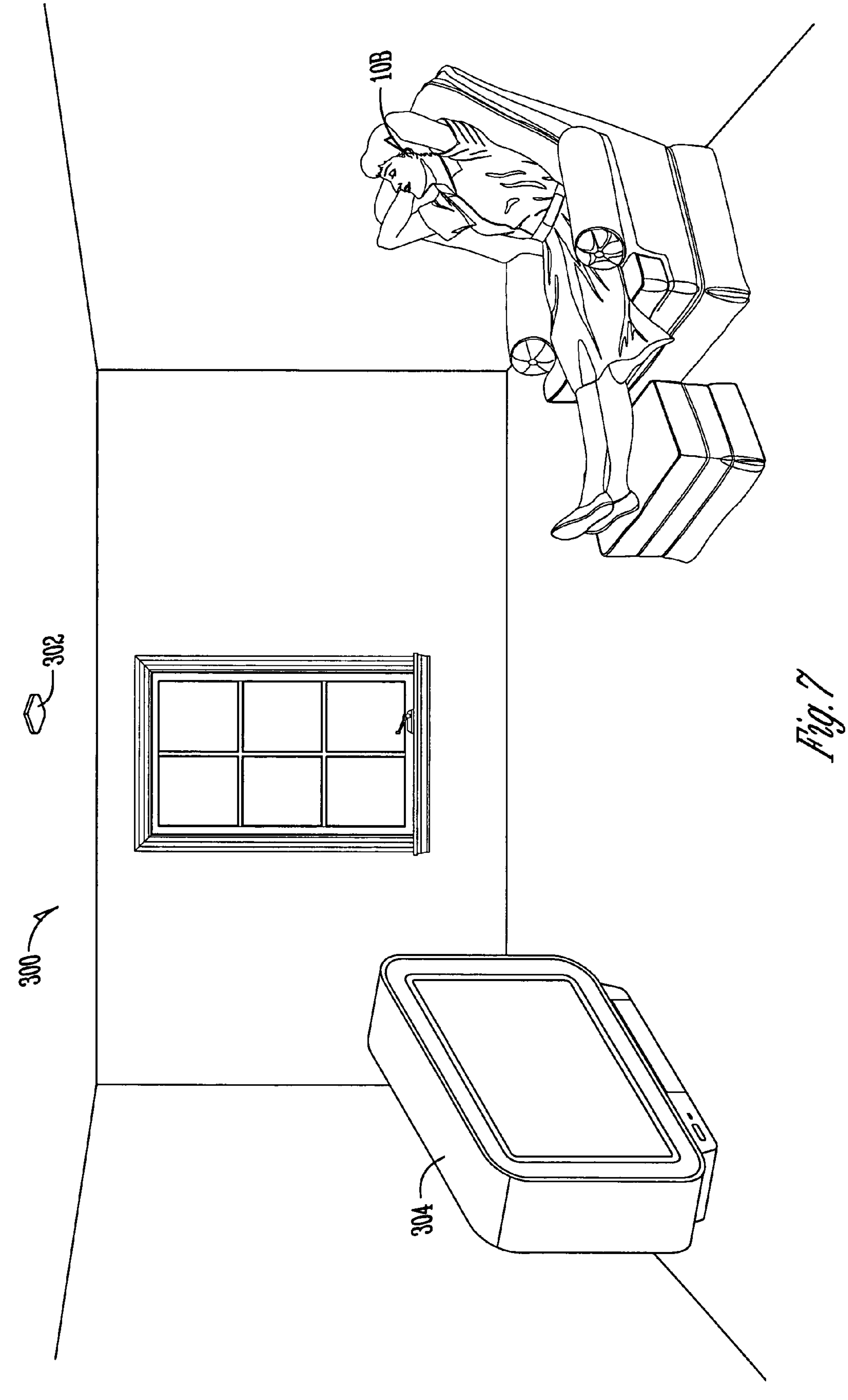
FIG. 7 is a pictorial representation of another embodiment of the invention.

FIG. 7 illustrates another use of the present invention. As shown in FIG. 7 an environment 300 such as in a home is shown. The home includes a network with network nodes such as 302. A user is shown enjoying themselves as they rest on a recliner and wear an earpiece 10B while watching television 304. The earpiece 10B provides audio sounds to the user. The present invention provides for audio from or associated with the television 304 to be communicated through the network and be transmitted from the network node 302 to the earpiece 10B. Thus the user can control the incoming sounds received at the earpiece. Multiple persons in the same room can be watching the same television, but each have their earpiece set to different volumes or have additional audio processing performed by their respective earpiece or earpieces to meet their own audiometric needs. Although in the embodiment shown, audio associated with the television is communicated through the network node 302, audio could also be communicated directly from the television with 304 with a short range transceiver.

Figure 8:
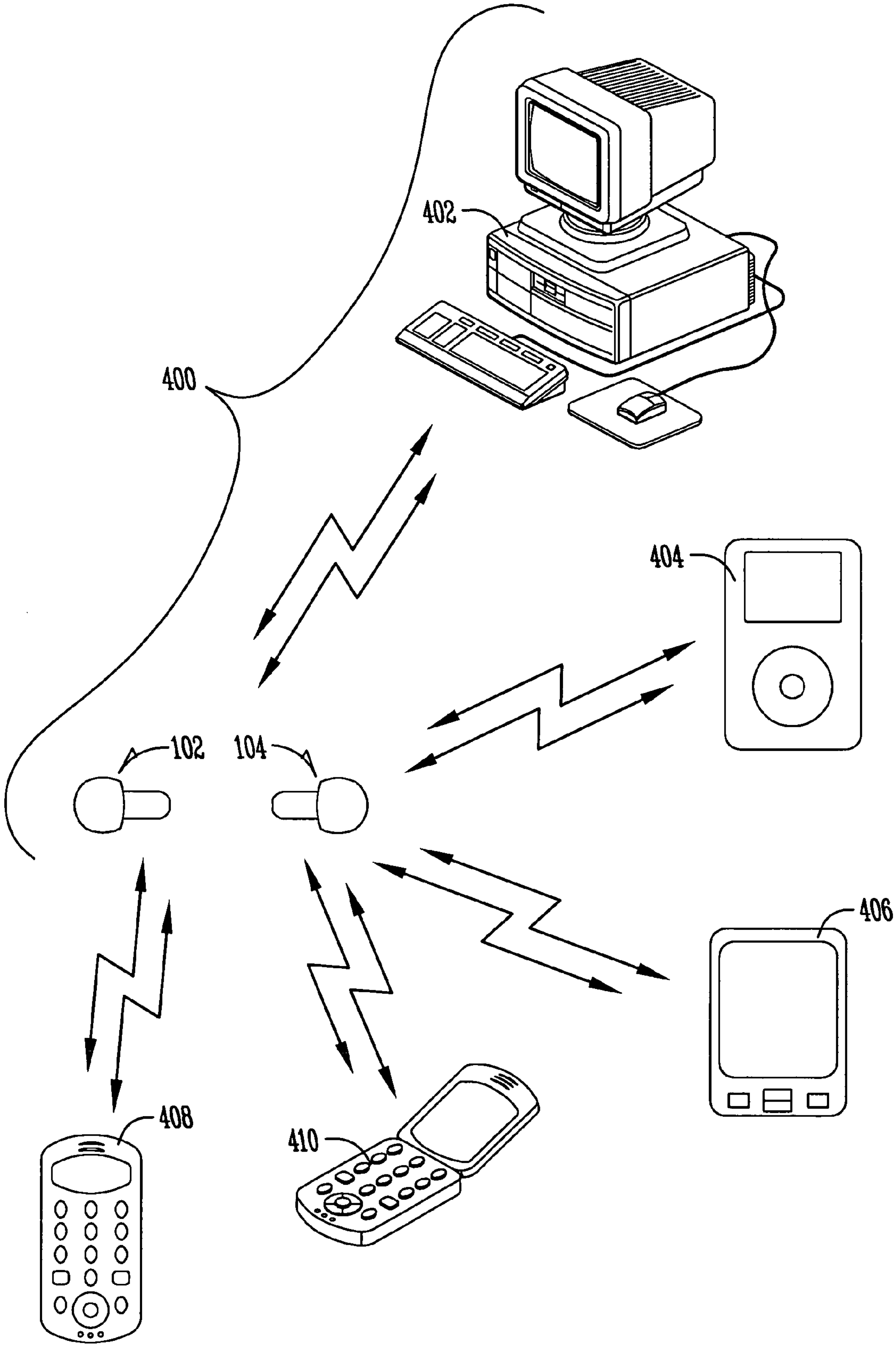
FIG. 8 is a diagram illustrating another embodiment of the invention.

FIG. 8 illustrates another embodiment of the invention. FIG. 8 shows different types of devices that may include short range transceivers and be audio sources or recipients of audio transmissions from one or both of earpieces 102, 104. In the system 400 shown, there is a computer 402, a portable entertainment device for audio and/or video 404, and a PDA 406, a candy bar type phone 408, and a flip type phone 410. Each of these devices or others may communicate with one or both of earpieces 102, 104.

A general description of the present invention as well as a preferred embodiment has been set forth above. Those skilled in the art will recognize and will be able to practice additional variations and the methods and devices described which fall within the teachings of this invention. Accordingly, all such modifications and additions are deemed to be within the scope of the invention which is to be limited only by the claims appended hereto.

What is claimed is:

1. A method for voice communication, comprising:
- sensing at least one channel of audio information from within a first external auditory canal of a first user with a first non-occlusive earpiece;
- sensing at least one channel of audio information from within a second external auditory canal of the first user with a second non-occlusive earpiece;
- producing an outgoing stereophonic audio signal based on the at least one channel of audio information from the first external auditory canal and the at least one channel of audio information from the second external auditory canal;
- wirelessly transmitting the outgoing stereophonic audio signal;
- wirelessly receiving an incoming stereophonic audio signal;
- transducing a first channel of the incoming stereophonic audio signal at a first speaker proximate a first external auditory canal of a second user with a first non-occlusive earpiece; and
- transducing a second channel of the incoming stereophonic audio signal at a second speaker proximate a second external auditory canal of the second user with a second non-occlusive earpiece.

2. The method of claim 1 wherein the outgoing stereophonic audio signal is transduced at a phone.

3. The method of claim 1 wherein the step of producing the outgoing stereophonic audio signal being performed at a personal electronic device.

4. The method of claim 3 wherein the step of wirelessly transmitting the outgoing stereophonic audio signal comprises wirelessly transmitting the outgoing stereophonic audio signal from the personal electronic device to a second personal electronic device.

5. The method of claim 4 further comprising transmitting the outgoing stereophonic audio signal from the second personal electronic device to one or more devices associated with the ears of a second user.

6. The method of claim 5 further comprising reproducing the at least one channel of audio information from the first external auditory canal of a user within a first auditory canal of a second user and reproducing the at least one channel of audio information from the second external auditory canal of the user within a second auditory canal of a second user.

7. The method of claim 4 wherein the personal electronic device is a phone and the second personal electronic device is a phone.

8. The method of claim 4 wherein the personal electronic device is a phone and the second personal electronic device is a computer.

9. The method of claim 4 wherein the personal electronic device is a phone and the second personal electronic device is an entertainment device.

10. The method of claim 4 wherein the personal electronic device is a phone and the second personal electronic device is a home area network.

11. The method of claim 5 wherein the one or more devices associated with the ears of a user includes a left ear earpiece and a right ear earpiece.

12. The method of claim 1 wherein the step of transducing at least one channel of audio information from within the first external auditory canal includes transducing with a bone conduction sensor disposed within the first external auditory canal.

13. The method of claim 12 wherein the step of transducing at least one channel of audio information from within the second external auditory canal includes transducing with a bone conduction sensor disposed within the second external auditory canal.

14. The method of claim 12 wherein the step of transducing at least one channel of audio information from within the first external auditory canal includes transducing with a bone conduction sensor disposed within the first external auditory canal and an air conduction sensor disposed within the first external auditory canal.

15. The method of claim 14 wherein the step of transducing at least one channel of audio information from within the second external auditory canal includes transducing with a bone conduction sensor disposed within the second external auditory canal and an air conduction sensor disposed within the second external auditory canal.

16. A method for stereophonic voice communication between a first user and a second user, comprising:
- sensing at least one channel of audio information proximate a first external auditory canal of the first user with a first nonocclusive earpiece;
- sensing at least one channel of audio information proximate a second external auditory canal of the first user with a second nonocclusive earpiece;
- wirelessly transmitting the at least one channel of audio information proximate the first external auditory canal of the first user and the at least one channel of audio information proximate the second external auditory canal of the first user;
- outputting at least one channel of audio information proximate a first external auditory canal of the second user with a first non-occlusive earpiece;
- outputting at least one channel of audio information proximate a second external auditory canal of the second user with a second non-occlusive earpiece.

17. The method of claim 16 further comprising adjusting the at least one channel of audio information from proximate the first external auditory canal of the first user and the at least one channel of audio information from proximate the second external auditory canal of the first user to accommodate audiometric settings associated with the second user.

18. The method of claim 16 wherein the step of sensing at least one channel of audio information from within a first external auditory canal of the first user is performed using a microphone position at least partially within the first external auditory canal of the first user.

19. The method of claim 16 wherein the step of outputting at least one channel of audio information proximate the first external auditory canal of the second user is performed using a speaker placed proximate the first external auditory canal of the second user.

20. A method comprising:

collecting a stereophonic representation of sound associated with a first user using one or more sensors positioned proximate each external auditory canal of the first user with a non-occlusive earpiece;

sending the stereophonic representation of sound to a voice communication device associated with the first user;

sending the stereophonic representation of sound from the voice communication device to a second user;

playing the stereophonic representation of sound for the second user proximate each external auditory canal of the second user with a non-occlusive ear piece.

21. The method of claim 20 wherein the step of playing the stereophonic representation of sound for the second user is performed using one or more speakers positioned proximate the external auditory canal of the user.

22. The method of claim 20 wherein the step of collecting a stereophonic representation of sound is performed using one or more sensors positioned within the external auditory canal of the user.

23. The method of claim 20 wherein the step of playing the stereophonic representation of sound for the second user is performed using one or more speakers positioned proximate the external auditory canal of the user.

24. The method of claim 20 wherein the voice communication device associated with the second user is adapted to adjust the stereophonic representation of sound to accommodate audiometric needs of the second user.

25. The method of claim 20 wherein the voice communication device associated with the second user is adapted to adjust the stereophonic representation of sound to accommodate audiometric settings associated with the second user.

* * * * *